United States Patent
Ogawa et al.

(10) Patent No.: US 11,130,974 B2
(45) Date of Patent: Sep. 28, 2021

(54) HYDROXYLATED FATTY ACID HOMOPOLYMER AND PRODUCTION METHOD THEREOF

(71) Applicants: KYOTO UNIVERSITY, Kyoto (JP); Noster Inc., Muko (JP)

(72) Inventors: Jun Ogawa, Kyoto (JP); Shigenobu Kishino, Kyoto (JP); Kohey Kitao, Muko (JP)

(73) Assignees: KYOTO UNIVERSITY, Kyoto (JP); Noster Inc., Muko (JP)

(*) Notice: Subject to any disclaimer, the term of this patent is extended or adjusted under 35 U.S.C. 154(b) by 0 days.

(21) Appl. No.: 16/642,282

(22) PCT Filed: Aug. 30, 2018

(86) PCT No.: PCT/JP2018/032249
§ 371 (c)(1),
(2) Date: Feb. 26, 2020

(87) PCT Pub. No.: WO2019/045011
PCT Pub. Date: Mar. 7, 2019

(65) Prior Publication Data
US 2021/0079432 A1    Mar. 18, 2021

(30) Foreign Application Priority Data
Aug. 31, 2017 (JP) .............................. JP2017-167595

(51) Int. Cl.
 C12P 7/64         (2006.01)
 C07C 69/732      (2006.01)
(52) U.S. Cl.
 CPC .......... *C12P 7/6436* (2013.01); *C07C 69/732* (2013.01)

(58) Field of Classification Search
 CPC ............................. C12P 7/6436; C12C 69/732
(Continued)

(56) References Cited

U.S. PATENT DOCUMENTS

2006/0217441 A1   9/2006  Akimoto et al.
2010/0285545 A1  11/2010  Gross et al.
(Continued)

FOREIGN PATENT DOCUMENTS

JP        6416591 A  *  1/1989
JP     S64-016591 A     1/1989
(Continued)

OTHER PUBLICATIONS

Hayes, D. G., Lipase-catalyzed synthesis and properties of estolides and their esters, J. Am. Oil Chem. Soc., 1995, vol. 72, No. 11, pp. 1309-1316.*
Hayes, D. G., The catalytic activity of lipases toward hydroxy fatty acids—a review, J. Am. Oil Chem. Soc., 1996, vol. 73, No. 5, pp. 543-549.*
(Continued)

*Primary Examiner* — Deborah D Carr
(74) *Attorney, Agent, or Firm* — Leydig, Voit & Mayer, Ltd.

(57) ABSTRACT

The present invention provides a derivative of hydroxylated fatty acid which has a high content of hydroxylated fatty acid, and permits easy ingestion and easy handling, and a production method thereof. The present invention provides a method for producing a homopolymer of hydroxylated fatty acid, including polymerizing the hydroxylated fatty acid by using an enzyme. The homopolymer of hydroxylated fatty acid is stabilized. In addition, a novel, utilizable homopolymer of hydroxylated fatty acid obtained by this production method is also provided.

16 Claims, 3 Drawing Sheets

(58) Field of Classification Search
USPC .......................................................... 514/219
See application file for complete search history.

(56) References Cited

U.S. PATENT DOCUMENTS

| | | | |
|---|---|---|---|
| 2015/0125911 A1 | 5/2015 | Ogawa et al. | |
| 2015/0342916 A1 | 12/2015 | Ogawa et al. | |
| 2016/0000739 A1 | 1/2016 | Ogawa et al. | |
| 2017/0022526 A1 | 1/2017 | Ogawa et al. | |
| 2018/0170854 A1 | 6/2018 | Yonejima et al. | |
| 2018/0318248 A1 | 11/2018 | Yonejima et al. | |

FOREIGN PATENT DOCUMENTS

| | | | | |
|---|---|---|---|---|
| JP | 5304966 A | * | 11/1993 | |
| JP | H05-304966 A | | 11/1993 | |
| JP | 2006-521368 A | | 9/2006 | |
| WO | WO 2013/168310 A1 | | 11/2013 | |
| WO | WO 2014/069227 A1 | | 5/2014 | |
| WO | WO 2014/129384 A1 | | 8/2014 | |
| WO | WO 2015/111699 A1 | | 7/2015 | |
| WO | WO 2016/151115 A1 | | 9/2016 | |
| WO | WO-2016151115 A1 | * | 9/2016 | ............... C12N 9/20 |
| WO | WO 2016/195016 A1 | | 12/2016 | |
| WO | WO 2016/195017 A1 | | 12/2016 | |

OTHER PUBLICATIONS

Todea, A., et al., Selectivity of lipases for estolides synthesis, Pure Appl. Chem., 2015, vol. 87, No. 1, pp. 51-58.*

Martin-Arjol, I., et al., Mono-estolide synthesis from trans 8-hydroxy-fatty acids by lipases in solvent-free media and their physical properties, J. Am. Oil Chem. Soc., 2015, vol. 92, pp. 1125-1141.*

Hayes et al., "Lipase-Catalyzed Synthesis and Properties of Estolides and Their Esters," *J. Am. Oil Chem. Soc.*, 72(11): 1309-1316 (1995).

Hayes et al., "The Catalytic Activity of Lipases Toward Hydroxy Fatty Acids—A Review," *J. Am. Oil Chem. Soc.*, 73(5): 543-549 (1996).

Martin-Arjol et al., "Mono-Estolide Synthesis from trans-8-Hydroxy-Fatty Acids by Lipases in Solvent-Free Media and Their Physical Properties," *J. Am. Oil Chem. Soc.*, 92: 1125-1141 (2015).

Miyamoto et al., "A Gut Microbial Metabolite of Linoleic Acid, 10-Hydroxy-cis-12-octadecenoic Acid, Ameliorates Intestinal Epithelial Barrier Impairment Partially via GPR40-MEK-ERK Pathway," *J. Biol. Chem.*, 290(5): 2902-2918 (2015).

Nagao et al., "Conjugated Fatty Acids in Food and Their Health Benefits," *J. Biosci. Bioeng.*, 100(2): 152-157 (2005).

Todea et al., "Selectivity of lipases for estolides synthesis," *Pure Appl. Chem.*, 87(1): 51-58 (2015).

Japanese Patent Office, International Search Report in International Patent Application No. PCT/JP2018/032249 (dated Oct. 23, 2018).

European Patent Office, Extended European Search Report in European Patent Application No. 18850755.2 (dated Apr. 30, 2021).

* cited by examiner

αHYA (sample)    αHYA homo-polymer    13HYA (sample)    13HYA homo-polymer    ricinoleic acid (sample)    ricinoleic acid homo-polymer

HYDROXYLATED FATTY ACID HOMOPOLYMER AND PRODUCTION METHOD THEREOF

CROSS-REFERENCE TO RELATED APPLICATIONS

This patent application is the U.S. national phase of International Patent Application No. PCT/JP2018/032249, filed Aug. 30, 2018, which claims the benefit of Japanese Patent Application No. 2017-167595, filed on Aug. 31, 2017, which are incorporated by reference in their entireties herein.

TECHNICAL FIELD

The present invention relates to a novel homopolymer of hydroxylated fatty acid and a production method thereof. The hydroxylated fatty acid is a fatty acid having at least one hydroxyl group. In the production method of the present invention, a homopolymer of hydroxylated fatty acid is obtained by a selective polymerization reaction of hydroxylated fatty acid utilizing an enzyme, while suppressing formation of intramolecular lactone by intramolecular dehydration. The present invention also provides a novel homopolymer of hydroxylated fatty acid. The homopolymer of hydroxylated fatty acid can be utilized as a medicament, a food or a chemical starting material.

BACKGROUND ART

In recent years, the physiological function of scarce fatty acid present only at a low ratio in the body has been attracting attention. For example, it has been reported that conjugated fatty acids such as conjugated linoleic acid and the like (non-patent document 1) and ω3 polyvalent unsaturated fatty acids such as eicosapentaenoic acid, docosahexaenoic acid and the like (patent document 1) have lipid metabolism improving effects, diabetes improving effects and the like. There is a high interest in ingesting those functional lipids from the diet, and products containing them such as foods, etc. are on the market.

One of the scarce fatty acids is a hydroxylated fatty acid having a hydroxyl group in the compound. The physiological functions thereof have not been analyzed sufficiently heretofore due to the absence of a suitable source of supply. Recently, however, a means for highly efficient and highly selective production by an enzymatic reaction using linoleic acid or the like, which is contained in a large amount in vegetable oil, as a starting material has been found (patent document 2). A method of supplying various hydroxylated fatty acids has been secured, along with which studies on the physiological functions thereof have been actively conducted. The present inventors particularly took note of 10-hydroxy-cis-12-octadecenoic acid (hereinafter to be also referred to as "HYA") among hydroxylated fatty acids, and reported that HYA has a lipid metabolism abnormality improving effect (patent document 3), an action to enhance intestinal immunity (patent document 4), a suppressive action on intestinal inflammations (non-patent document 2) and the like.

Since it has become easy to obtain high purity HYA as described above, if HYA can be ingested easily, effective utilization of HYA is expected to be promoted by utilizing its physiological functions. In addition to physiological activity, HYA can also be used as a starting material for sebacic acid and is attracting attention as a starting material for chemical products. On the other hand, since the melting point of HYA is about 25° C. ("about" here means±1° C.) and HYA is solid (or partially melted state) at ambient temperature, there was a problem that it is inferior to liquid in the ease of ingestion and handleability in adding to or mixing with other liquid or solid food components. In an attempt to solve this problem, the present inventors reported triglyceridation and alkyl esterification thereof (patent documents 5 and 6). However, since triglyceridation and alkyl esterification require reaction with glycerol or alcohol besides hydroxylated fatty acid, the proportion of the structural unit in HYA-derived molecules becomes small, and it is not the form of a starting material that provides HYA at a high content.

On the other hand, a hydroxylated fatty acid derivative capable of solving the above-mentioned problems has not been reported heretofore.

DOCUMENT LIST

Patent Documents patent document 1: National Publication of International Patent Application No. 2006-521368
patent document 2: WO 2013/168310
patent document 3: WO 2014/069227
patent document 4: WO 2014/129384
patent document 5: WO 2016/195016
patent document 6: WO 2016/195017

Non-Patent Documents non-patent document 1: Nagao K, J. Biosci. Bioeng., 2005, vol. 100, no. 2, p. 152-157
non-patent document 2: Junki Miyamoto et al., J. Biol. Chem., 2015, 290(5), 2902-2918

SUMMARY OF THE INVENTION

Problems to be Solved by the Invention

The problem of the present invention is provision of a novel derivative of hydroxylated fatty acid which has a high content of hydroxylated fatty acid, and permits easy ingestion and easy handling, and a production method thereof.

Means of Solving the Problems

The present inventors have conducted intensive studies in view of the above-mentioned problems and clarified a method for multimerizing a hydroxylated fatty acid itself under normal pressure (conditions free of reduced pressure or pressurization) by using an enzyme. Furthermore, the homopolymer of hydroxylated fatty acid produced by this method showed an increased proportion of a hydroxylated fatty acid-derived structural unit in the molecules, as compared with triacylglycerides and alkyl ester. As a result, they have successfully provided a multimerized, stable and novel substance and completed the present invention.

That is, the present invention provides the following.
[1] A method for producing a homopolymer of hydroxylated fatty acid, comprising polymerizing the hydroxylated fatty acid by using an enzyme.
[2] The method of [1], wherein the enzyme is a lipase.
[3] The method of [1], wherein the enzyme is a lipase derived from a microorganism belonging to the genus *Candida*.

[4] The method of [1], wherein the enzyme is a lipase derived from *Candida cylindracea* or *Candida rugosa*.
[5] The method of any one of [1] to [4], wherein the homopolymer of hydroxylated fatty acid is a dimer to decamer.
[6] The method of any one of [1] to [5], wherein the hydroxylated fatty acid is
(1) a fatty acid having 18 carbon atoms and a hydroxyl group at the 10-position, the 12-position or the 13-position,
(2) a fatty acid having 20 carbon atoms and a hydroxyl group at the 12-position or the 15-position,
(3) a fatty acid having 14 or 16 carbon atoms and a hydroxyl group at the 10-position, or
(4) a fatty acid having 22 carbon atoms and a hydroxyl group at the 14-position.
[7] The method of [6], wherein the hydroxylated fatty acid is a fatty acid having 18 carbon atoms and a hydroxyl group at the 10-position, the 12-position or the 13-position.
[8] The method of [7], wherein the hydroxylated fatty acid is
10-hydroxy-cis-12-octadecenoic acid,
10-hydroxy-cis-12,cis-15-octadecadienoic acid,
10-hydroxy-cis-6,cis-12-octadecadienoic acid,
10-hydroxy-cis-6,cis-12,cis-15-octadecatrienoic acid,
10-hydroxyoctadecanoic acid,
10-hydroxy-cis-15-octadecenoic acid,
10-hydroxy-cis-6-octadecenoic acid,
10-hydroxy-cis-6,cis-15-octadecadienoic acid,
10-hydroxy-trans-11-octadecenoic acid,
10-hydroxy-trans-11,cis-15-octadecadienoic acid,
10-hydroxy-cis-6,trans-11-octadecadienoic acid,
10-hydroxy-cis-6,trans-11,cis-15-octadecatrienoic acid, ricinoleic acid,
12-hydroxyoctadecanoic acid,
13-hydroxy-cis-9-octadecenoic acid,
13-hydroxy-cis-9,cis-15-octadecadienoic acid,
13-hydroxy-cis-6,cis-9-octadecadienoic acid,
13-hydroxy-cis-6,cis-9,cis-15-octadecatrienoic acid,
13-hydroxy-cis-5,cis-9-octadecadienoic acid, or
13-hydroxy-trans-5,cis-9-octadecadienoic acid.
[9] The method of [6], wherein the hydroxylated fatty acid is a fatty acid having 20 carbon atoms and a hydroxyl group at the 12-position or the 15-position.
[10] The method of [9], wherein the hydroxylated fatty acid is
12-hydroxy-cis-14-eicosenoic acid,
12-hydroxy-cis-14,cis-17-eicosadienoic acid,
12-hydroxy-cis-8,cis-14-eicosadienoic acid,
12-hydroxy-cis-5,cis-8-eicosadienoic acid,
12-hydroxy-cis-8,cis-14,cis-17-eicosatrienoic acid,
12-hydroxy-cis-5,cis-8,cis-14-eicosatrienoic acid,
15-hydroxy-cis-11-eicosenoic acid,
15-hydroxy-cis-11,cis-17-eicosadienoic acid,
15-hydroxy-cis-8,cis-11-eicosadienoic acid,
15-hydroxy-cis-8,cis-11,cis-17-eicosatrienoic acid,
15-hydroxy-cis-5,cis-8,cis-11-eicosatrienoic acid,
15-hydroxy-cis-5,cis-11-eicosadienoic acid, or
15-hydroxy-cis-5,cis-11,cis-17-eicosatrienoic acid.
[11] The method of [6], wherein the hydroxylated fatty acid is
10-hydroxytetradecanoic acid,
10-hydroxyhexadecanoic acid, or
14-hydroxy-cis-4,cis-7,cis-10,cis-16,cis-19-docosapentaenoic acid.
[12] A homopolymer as a dimer to a decamer of any one hydroxylated fatty acid selected from the following hydroxylated fatty acids:
10-hydroxy-cis-12-octadecenoic acid,
10-hydroxy-cis-12,cis-15-octadecadienoic acid,
10-hydroxy-cis-6,cis-12-octadecadienoic acid,
10-hydroxy-cis-6,cis-12,cis-15-octadecatrienoic acid,
10-hydroxyoctadecanoic acid,
10-hydroxy-cis-15-octadecenoic acid,
10-hydroxy-cis-6-octadecenoic acid,
10-hydroxy-cis-6,cis-15-octadecadienoic acid,
10-hydroxy-trans-11-octadecenoic acid,
10-hydroxy-trans-11,cis-15-octadecadienoic acid,
10-hydroxy-cis-6,trans-11-octadecadienoic acid,
10-hydroxy-cis-6,trans-11,cis-15-octadecatrienoic acid,
13-hydroxy-cis-9-octadecenoic acid,
13-hydroxy-cis-9,cis-15-octadecadienoic acid,
13-hydroxy-cis-6,cis-9-octadecadienoic acid,
13-hydroxy-cis-6,cis-9,cis-15-octadecatrienoic acid,
13-hydroxy-cis-5,cis-9-octadecadienoic acid,
13-hydroxy-trans-5,cis-9-octadecadienoic acid,
12-hydroxy-cis-14-eicosenoic acid,
12-hydroxy-cis-14,cis-17-eicosadienoic acid,
12-hydroxy-cis-8,cis-14-eicosadienoic acid,
12-hydroxy-cis-5,cis-8-eicosadienoic acid,
12-hydroxy-cis-8,cis-14,cis-17-eicosatrienoic acid,
12-hydroxy-cis-5,cis-8,cis-14-eicosatrienoic acid,
15-hydroxy-cis-11-eicosenoic acid,
15-hydroxy-cis-11,cis-17-eicosadienoic acid,
15-hydroxy-cis-8,cis-11-eicosadienoic acid,
15-hydroxy-cis-8,cis-11,cis-17-eicosatrienoic acid,
15-hydroxy-cis-5,cis-8,cis-11-eicosatrienoic acid,
15-hydroxy-cis-5,cis-11-eicosadienoic acid,
15-hydroxy-cis-5,cis-11,cis-17-eicosatrienoic acid,
10-hydroxytetradecanoic acid,
10-hydroxyhexadecanoic acid, and
14-hydroxy-cis-4,cis-7,cis-10,cis-16,cis-19-docosapentaenoic acid.
[13] The homopolymer of [12], wherein the homopolymer is a dimer, a trimer or a tetramer of 10-hydroxy-cis-12-octadecenoic acid represented by the formula

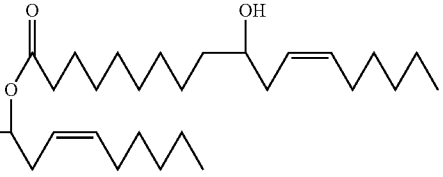

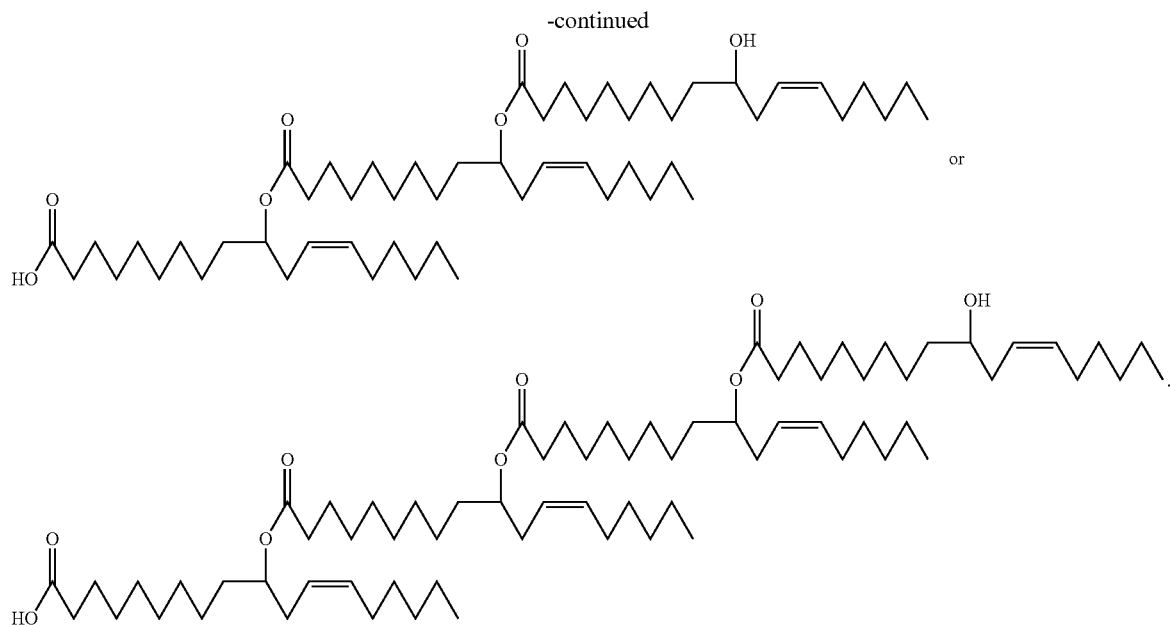

[14] A composition comprising the homopolymer of [12] or [13].

Effect of the Invention

According to the present invention, a hydroxylated fatty acid can be polymerized by an enzyme (e.g., lipase) to give a multimer (homopolymer), and the properties thereof can be stabilized by forming a multimer. When a polymerized multimer is ingested in a food, an ester bond formed by polymerization is decomposed by digestive enzymes such as lipase and the like to provide the original hydroxylated fatty acid and allow for its action. Since various methods for using hydroxylated fatty acid are being found, it is industrially extremely useful to stabilize the properties thereof and form an easily handleable substance thereof. Using an enzyme (e.g., lipase), moreover, a selective polymerization reaction of a hydroxylated fatty acid can be performed while suppressing formation of an intramolecular lactone by intramolecular dehydration.

DESCRIPTION OF EMBODIMENTS

Figure 1:
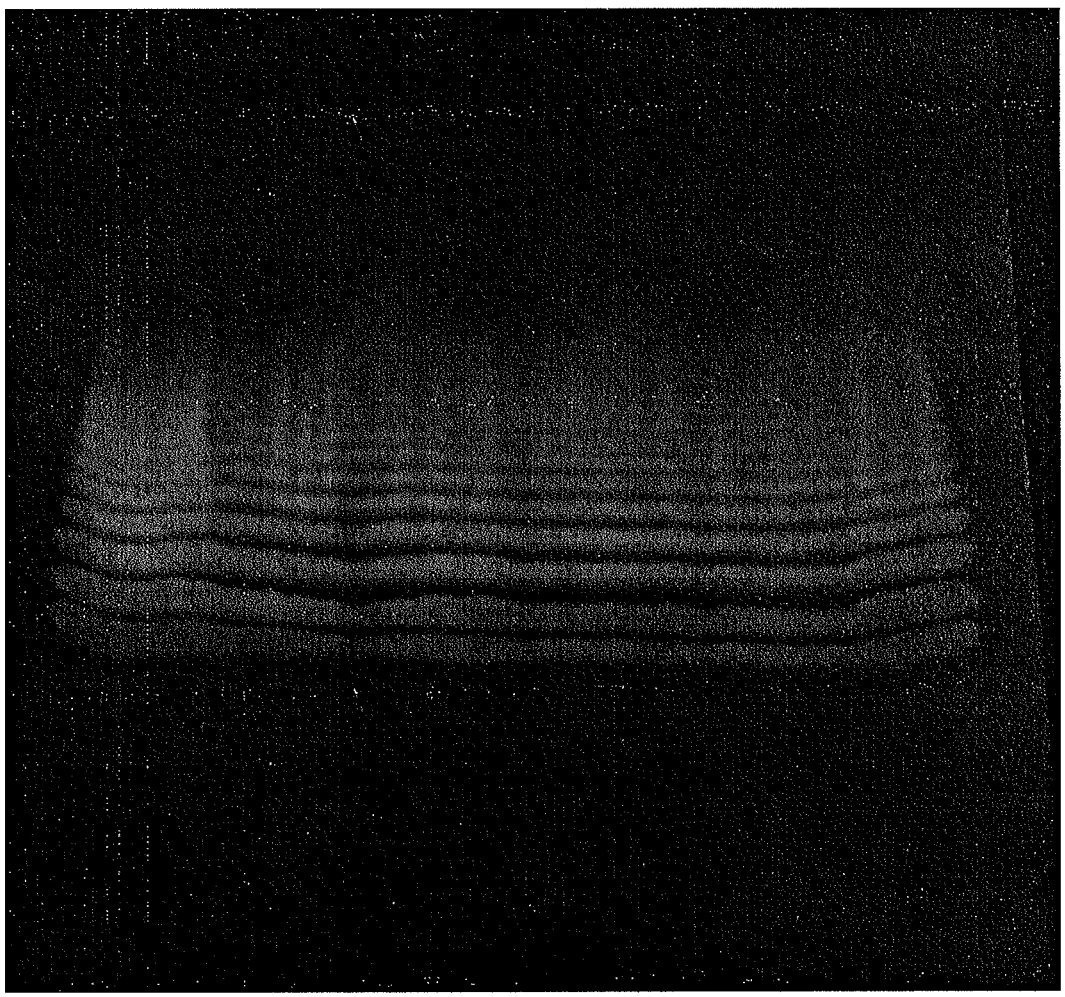
FIG. 1 is a photograph showing the results of thin layer chromatography in Example 2.

The present invention is explained in detail in the following.

(Definition)

In the present specification, "fatty acid" means a straight chain or branched chain aliphatic hydrocarbon having one carboxy group. The fatty acid may have one or two or more unsaturated bonds in the aliphatic hydrocarbon chain thereof. A part of the aliphatic hydrocarbon chain may be substituted by a hydroxyl group or an oxo group (=O). While the range of the number of the carbon atoms of "fatty acid" is not particularly limited, it is preferably 6-26, more preferably 8-24, further preferably 8-22, most preferably 14-22.

In the present specification, the "hydroxylated fatty acid" means a fatty acid having at least one hydroxyl group besides the hydroxyl group in the carboxy group.

In the present specification, the "homopolymer of hydroxylated fatty acid" means a substance formed into a multimer by polymerizing, by an intermolecular ester bond, a carboxy group in a hydroxylated fatty acid molecule with a hydroxyl group in another hydroxylated fatty acid molecule having the same molecular structure.

Example, trimer of 10-hydroxy-cis-12-octadecenoic acid

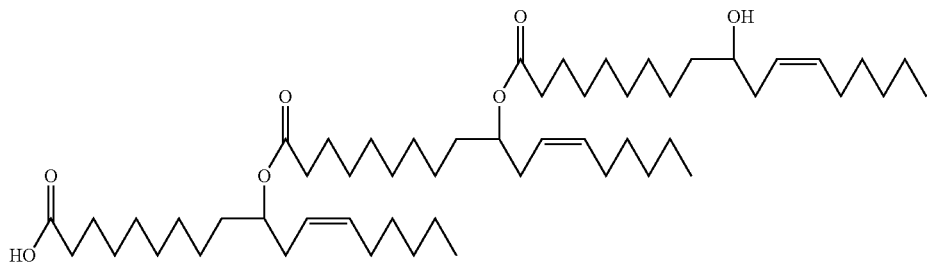 [SMILES: CCCCC/C=C\CC(O)CCCCCCCCC(=O)OC(C/C=C\CCCCC)CCCCCCCCC(=O)OC(C/C=C\CCCCC)CCCCCCCCC(=O)O]

The present invention provides a production method of a homopolymer of hydroxylated fatty acid, which includes polymerizing the hydroxylated fatty acid using an enzyme (e.g., lipase).

The production method of the present invention causes self-polymerization of hydroxylated fatty acid using an enzyme (e.g., lipase). Lipase is a generic term for enzymes that decompose triglyceride and release fatty acid. The enzymes are also used in the synthesis of terpene alcohol ester, synthesis of cholesterol ester and the like since they reversely catalyze esterification and enzymatic characteristics thereof can be utilized. Lipase is an enzyme that preferentially catalyzes hydrolysis in the presence of water. To perform a condensation reaction involving dehydration, it is necessary to remove water under reduced pressure. Thus, lipase requires various devices for industrial use as a dehydration reaction catalyst. Chemical dehydration requires high temperatures, and intramolecular dehydration and deterioration of the compound itself are feared. Therefore, it is not known that lipase catalyzes the intermolecular esterification of carboxy group of hydroxylated fatty acid and hydroxyl group of the same molecule under normal pressure (without reduced pressure) to form a multimer, and such reaction was considered to be difficult to occur.

The reaction in the production method of the present invention (hereinafter to be referred to as "this reaction") is specifically the following reaction.

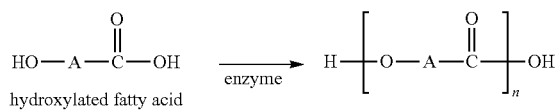

wherein A is a partial structure of hydroxylated fatty acid wherein carboxy group and hydroxyl group are removed, and n is 2 or more.

The homopolymer of hydroxylated fatty acid produced by the method of the present invention is preferably a dimer to an icosamer (n is 2-20), more preferably a dimer to a decamer (n is 2-10).

The enzyme to be used for this reaction is preferably lipase, more preferably a lipase derived from a microorganism, particularly preferably a lipase derived from a microorganism belonging to the genus *Candida*. Furthermore preferred is a lipase derived from *Candida cylindracea* or *Candida rugosa*.

The lipase derived from *Candida cylindracea* includes a plurality of isozymes, and Lip1, Lip2, Lip3, Lip4, Lip5 and the like are known. In the present invention, Lip4 and Lip5 among them show high reaction efficiency; however, any isozyme may be used and a mixture thereof may also be used.

The lipase derived from *Candida rugosa* includes a plurality of isozymes, and Lip1, Lip2, Lip3, Lip4, Lip5 and the like are known. In the present invention, Lip4 and Lip5 among them show high reaction efficiency; however, any isozyme may be used and a mixture thereof may also be used.

Microorganism-derived lipases can be purchased as a commercially available product from Amano Enzyme Inc., Meito Sangyo Co., Ltd., Novozymes A/S, Sigma-Aldrich Co. LLC and the like. For example, lipase AY "Amano" 30SD (derived from *Candida cylindracea*) manufactured by Amano Enzyme Inc. and the like can be mentioned.

In this reaction, a "cofactor" may also be used.

This reaction is desirably performed at a preferable temperature and a preferable pH for the enzyme (e.g., lipase). For example, the reaction temperature is 20-45° C., preferably 35-39° C. The pH of the reaction mixture is, for example, pH 4-11, preferably pH 7-9. While the reaction time is not particularly limited, it is, for example, 30 min-48 hr, preferably 60 min-36 hr.

The amount of enzyme (e.g., lipase) to be used in this reaction is not particularly limited. It is preferably 1 wt % to 100 wt %, more preferably 3 wt % to 50 wt %, particularly preferably 5 wt % to 10 wt %, based on hydroxylated fatty acid.

This reaction can be performed in the presence of water but it is not limited thereto. The amount of water to be used in this reaction is preferably 0.3 g to 10 g, more preferably 0.5 g to 5 g, per 1 g of hydroxylated fatty acid. In this reaction, an organic solvent may also be used as necessary. This reaction can be performed under normal pressure (conditions without reduced pressure or pressurization).

The enzyme to be used in this reaction may be immobilized by various carriers or may be of a free type. The immobilized ones can be recovered and used repeatedly. The above-mentioned enzymes may be purified or crude products.

The produced homopolymer can be isolated and purified using a conventionally-used separation means such as chromatography, distillation, extraction and the like.

The substrate of this reaction only needs to be hydroxylated fatty acid. For example,
(1) a fatty acid having 18 carbon atoms and a hydroxyl group at the 10-position, the 12-position or the 13-position,
(2) a fatty acid having 20 carbon atoms and a hydroxyl group at the 12-position or the 15-position,
(3) a fatty acid having 14 or 16 carbon atoms and a hydroxyl group at the 10-position,
(4) a fatty acid having 22 carbon atoms and a hydroxyl group at the 14-position, and the like can be mentioned.

The fatty acid here means a straight chain fatty acid which is a straight chain aliphatic hydrocarbon having one carboxy group.

The fatty acid having 18 carbon atoms and a hydroxyl group at the 10-position, the 12-position or the 13-position may be a saturated fatty acid or an unsaturated fatty acid.

Examples of the fatty acid having 18 carbon atoms and a hydroxyl group at the 10-position include a saturated fatty acid having 18 carbon atoms and a hydroxyl group at the 10-position; an unsaturated fatty acid having 18 carbon atoms, a hydroxyl group at the 10-position, and at least one (preferably 1, 2 or 3) cis double bond at the 6-position, the 12-position, the 15-position; and an unsaturated fatty acid having 18 carbon atoms, a hydroxyl group at the 10-position, and at least one (preferably 1, 2 or 3) cis or trans double bond at the 6-position, the 11-position, the 15-position. Specifically, for example,
10-hydroxy-cis-12-octadecenoic acid (HYA),
10-hydroxy-cis-12,cis-15-octadecadienoic acid (hereinafter to be also referred to as "αHYA"),
10-hydroxy-cis-6,cis-12-octadecadienoic acid (hereinafter to be also referred to as "γHYA"),
10-hydroxy-cis-6,cis-12,cis-15-octadecatrienoic acid (hereinafter to be also referred to as "sHYA"),
10-hydroxyoctadecanoic acid (hereinafter to be also referred to as "HYB"),
10-hydroxy-cis-15-octadecenoic acid (hereinafter to be also referred to as "αHYB"),
10-hydroxy-cis-6-octadecenoic acid (hereinafter to be also referred to as "γHYB"), 10-hydroxy-cis-6,cis-15-octadecadienoic acid (hereinafter to be also referred to as "sHYB"),
10-hydroxy-trans-11-octadecenoic acid (hereinafter to be also referred to as "HYC"),
10-hydroxy-trans-11,cis-15-octadecadienoic acid (hereinafter to be also referred to as "αHYC"),
10-hydroxy-cis-6,trans-11-octadecadienoic acid (hereinafter to be also referred to as "γHYC"), or
10-hydroxy-cis-6,trans-11,cis-15-octadecatrienoic acid (hereinafter to be also referred to as "sHYC") can be mentioned.

Examples of the fatty acid having 18 carbon atoms and a hydroxyl group at the 12-position include a saturated fatty acid having 18 carbon atoms and a hydroxyl group at the 12-position; and an unsaturated fatty acid having 18 carbon atoms, a hydroxyl group at the 12-position, and a cis double bond at the 9-position. Specifically, for example, 12-hydroxyoctadecanoic acid and ricinoleic acid can be mentioned.

Examples of the fatty acid having 18 carbon atoms and a hydroxyl group at the 13-position include a saturated fatty acid having 18 carbon atoms and a hydroxyl group at the 13-position; and an unsaturated fatty acid having 18 carbon atoms, a hydroxyl group at the 13-position, and at least one (preferably 1, 2 or 3) cis or trans double bond at the 5-position, the 6-position, the 9-position, the 15-position. Specifically, for example,
13-hydroxy-cis-9-octadecenoic acid (hereinafter to be also referred to as "13HYA"),
13-hydroxy-cis-9,cis-15-octadecadienoic acid (hereinafter to be also referred to as "13αHYA"),
13-hydroxy-cis-6,cis-9-octadecadienoic acid (hereinafter to be also referred to as "13γHYA"),
13-hydroxy-cis-6,cis-9,cis-15-octadecatrienoic acid,
13-hydroxy-cis-5,cis-9-octadecadienoic acid, and
13-hydroxy-trans-5,cis-9-octadecadienoic acid can be mentioned.

The fatty acid having 20 carbon atoms and a hydroxyl group at the 12-position or the 15-position may be a saturated fatty acid or an unsaturated fatty acid.

Examples of the fatty acid having 20 carbon atoms and a hydroxyl group at the 12-position include a saturated fatty acid having 20 carbon atoms and a hydroxyl group at the 12-position; and an unsaturated fatty acid having 20 carbon atoms, a hydroxyl group at the 12-position, and at least one (preferably 1, 2 or 3) cis double bond at the 5-position, the 8-position, the 14-position, the 17-position. Specifically, for example,
12-hydroxy-cis-14-eicosenoic acid,
12-hydroxy-cis-14,cis-17-eicosadienoic acid,
12-hydroxy-cis-8,cis-14-eicosadienoic acid,
12-hydroxy-cis-5,cis-8-eicosadienoic acid,
12-hydroxy-cis-8,cis-14,cis-17-eicosatrienoic acid, and
12-hydroxy-cis-5,cis-8,cis-14-eicosatrienoic acid can be mentioned.

Examples of the fatty acid having 20 carbon atoms and a hydroxyl group at the 15-position include a saturated fatty acid having 20 carbon atoms and a hydroxyl group at the 15-position; and an unsaturated fatty acid having 20 carbon atoms, a hydroxyl group at the 15-position, and at least one (preferably 1, 2 or 3) cis double bond at the 5-position, the 8-position, the 11-position, the 17-position. Specifically, for example,
15-hydroxy-cis-11-eicosenoic acid,
15-hydroxy-cis-11,cis-17-eicosadienoic acid,
15-hydroxy-cis-8,cis-11-eicosadienoic acid,
15-hydroxy-cis-8,cis-11,cis-17-eicosatrienoic acid,
15-hydroxy-cis-5,cis-8,cis-11-eicosatrienoic acid,
15-hydroxy-cis-5,cis-11-eicosadienoic acid, and
15-hydroxy-cis-5,cis-11,cis-17-eicosatrienoic acid can be mentioned.

The fatty acid having 14 or 16 carbon atoms and a hydroxyl group at the 10-position may be a saturated fatty acid or an unsaturated fatty acid.

Examples of the fatty acid having 14 or 16 carbon atoms and a hydroxyl group at the 10-position include a saturated fatty acid having 14 or 16 carbon atoms and a hydroxyl group at the 10-position. Specifically, for example, 10-hydroxytetradecanoic acid, and 10-hydroxyhexadecanoic acid can be mentioned.

The fatty acid having 22 carbon atoms and a hydroxyl group at the 14-position may be a saturated fatty acid or an unsaturated fatty acid.

Examples of the fatty acid having 22 carbon atoms and a hydroxyl group at the 14-position include a saturated fatty acid having 22 carbon atoms and a hydroxyl group at the 14-position; and an unsaturated fatty acid having 22 carbon atoms, a hydroxyl group at the 14-position, and at least one (preferably 1, 2, 3, 4 or 5) cis double bond at the 4-position, the 7-position, the 10-position, the 16-position, the 19-position. Specifically, for example, 14-hydroxy-cis-4,cis-7,cis-10,cis-16,cis-19-docosapentaenoic acid can be mentioned.

The hydroxylated fatty acid to be used in this reaction can be prepared by the methods described in WO 2013/168310, WO 2015/111699 and the like. Alternatively, a commercially available product may also be used.

Examples of the homopolymer of hydroxylated fatty acid produced by this reaction include
dimmer of HYA,
trimer of HYA,
tetramer to decamer of HYA,
dimer to decamer of αHYA,
dimer to decamer of γHYA,
dimer to decamer of sHYA,
dimer to decamer of HYB,
dimer to decamer of αHYB,
dimer to decamer of γHYB,
dimer to decamer of sHYB,
dimer to decamer of HYC,
dimer to decamer of αHYC,
dimer to decamer of γHYC,
dimer to decamer of sHYC,
dimer to decamer of ricinoleic acid,
dimer to decamer of 12-hydroxyoctadecanoic acid,
dimer to decamer of 13HYA,
dimer to decamer of 13αHYA,
dimer to decamer of 13γHYA,
dimer to decamer of 13-hydroxy-cis-6,cis-9,cis-15-octadecatrienoic acid,
dimer to decamer of 13-hydroxy-cis-5,cis-9-octadecadienoic acid,
dimer to decamer of 13-hydroxy-trans-5,cis-9-octadecadienoic acid,
dimer to decamer of 12-hydroxy-cis-14-eicosenoic acid,
dimer to decamer of 12-hydroxy-cis-14,cis-17-eicosadienoic acid,
dimer to decamer of 12-hydroxy-cis-8,cis-14-eicosadienoic acid,
dimer to decamer of 12-hydroxy-cis-5,cis-8-eicosadienoic acid,
dimer to decamer of 12-hydroxy-cis-8,cis-14,cis-17-eicosatrienoic acid,
dimer to decamer of 12-hydroxy-cis-5,cis-8,cis-14-eicosatrienoic acid, dimer to decamer of 15-hydroxy-cis-11-eicosenoic acid,
dimer to decamer of 15-hydroxy-cis-11,cis-17-eicosadienoic acid,
dimer to decamer of 15-hydroxy-cis-8,cis-11-eicosadienoic acid,
dimer to decamer of 15-hydroxy-cis-8,cis-11,cis-17-eicosatrienoic acid,
dimer to decamer of 15-hydroxy-cis-5,cis-8,cis-11-eicosatrienoic acid,
dimer to decamer of 15-hydroxy-cis-5,cis-11-eicosadienoic acid,
dimer to decamer of 15-hydroxy-cis-5,cis-11,cis-17-eicosatrienoic acid,
dimer to decamer of 10-hydroxytetradecanoic acid,
dimer to decamer of 10-hydroxyhexadecanoic acid,
dimer to decamer of 14-hydroxy-cis-4,cis-7,cis-10,cis-16,cis-19-docosapentaenoic acid and the like. These homopolymers of hydroxylated fatty acid are novel hydroxylated fatty acid derivatives having structures not known to date.

For example, the homopolymer of HYA is represented by the following formula:

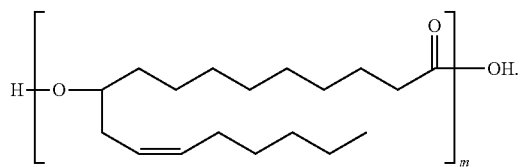

The homopolymer of αHYA, the homopolymer of 13HYA, and the homopolymer of ricinoleic acid are respectively represented by the following formulas.

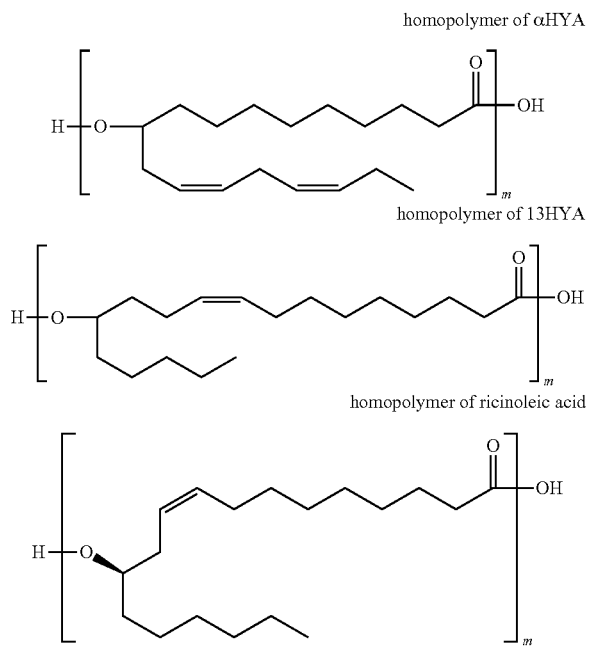

homopolymer of αHYA homopolymer of 13HYA homopolymer of ricinoleic acid wherein m is two or more, preferably 2-20, more preferably 2-10, particularly preferably 2-4.

The homopolymer of hydroxylated fatty acid of the present invention may be each isolated homopolymer, or a mixture of homopolymers. For example, the description "dimer to decamer" means a dimer, a trimer, a tetramer, a pentamer, a hexamer, a heptamer, an octamer, a nonamer, or a decamer, or a mixture of at least two selected from a dimer, a trimer, a tetramer, a pentamer, a hexamer, a heptamer, an octamer, a nonamer, and a decamer.

When the homopolymer of hydroxylated fatty acid obtained by the present invention is decomposed in the body by an enzyme such as lipase and the like, it becomes a free hydroxylated fatty acid. Free hydroxylated fatty acid is known to have a metabolism improving effect (improving effect on metabolism of lipid, sugar, energy), an intestine protection action, an anti-inflammatory action and the like (the aforementioned non-patent document 2, WO 2014/069227, WO 2014/129384, WO 2015/111700, WO 2015/111701). Thus, a homopolymer of hydroxylated fatty acid can be utilized as a stabilized precursor of hydroxylated fatty acid.

The homopolymer of hydroxylated fatty acid obtained by the present invention is used by blending in, for example, medicament, food, cosmetics based on conventionally-known physiological activities of free hydroxylated fatty acids.

The present invention provides a composition (including edible oil, food or food additive, pharmaceutical composition, cosmetics or cosmetics additive, feed or feed additive) containing the homopolymer of hydroxylated fatty acid of the present invention. The content of the homopolymer of hydroxylated fatty acid in the composition is generally 1 wt %-99.9 wt %, preferably 10 wt %-90 wt %, more preferably 20 wt %-80 wt %, based on the total amount of the composition.

When the homopolymer of hydroxylated fatty acid of the present invention is used as an edible oil, it can contain, for example, general components (food additive etc.) used for edible oil. Examples of such components include emulsifier, oxidation/degradation inhibitor, crystal adjuster and the like. Examples of the emulsifier include glycerol fatty acid ester, polyglycerol fatty acid ester, sucrose fatty acid ester, polyglycerol condensed ricinoleic acid ester, sorbitan fatty acid ester, propyleneglycol fatty acid ester, polyoxyethylene sorbitan fatty acid ester, organic acid monoglyceride and the like. Examples of the oxidation/degradation inhibitor include tocopherols, flavone derivative, kojic acid, gallic acid derivative, catechin and ester thereof, lignans such as sesamine and the like, fukiic acid, gossypol, sesamol, terpenes, silicone and the like. Examples of the crystal adjuster include triacylglycerol, diacylglycerol, waxes, sterol esters and the like. In addition, spice, coloring component and the like can also be added. Examples of the spice include capsaicin, anethole, eugenol, cineol, zingerone and the like. Examples of the coloring component include carotene, astaxanthin and the like.

While the content of the homopolymer of hydroxylated fatty acid in edible oil is not particularly limited, it is generally not less than 5 wt %, preferably not less than 20 wt %, more preferably not less than 50 wt %, based on the total amount of the edible oil.

When the homopolymer of hydroxylated fatty acid of the present invention is used as a food or a food additive, the form of the food is not particularly limited as long as it permits oral ingestion, such as solution, suspension, powder, solid formed article and the like. Specific examples include supplement (powder, granule, soft capsule, hard capsule, tablet, chewable tablet, quick-integrating tablet, syrup, liquid etc.), drinks (carbonated drinks, lactic drinks, sports drinks, fruit juice drinks, vegetable drinks, soymilk drink, coffee drinks, tea drinks, powder drinks, concentration drinks, nutritional beverage, alcohol drinks etc.), confectionery (gummi candy, jelly, gum, chocolate, cookie, candy, caramel candy, Japanese confectionery, snack food etc.), table-ready foods (instant noodles, retort food, canned food, microwave food, instant soup, miso soup, freeze-dry food etc.), oil, fats and oils food (mayonnaise, dressing, butter, cream, margarine etc.), wheat flour product (bread, pasta, noodle, cake mixture, breadcrumbs etc.), seasoning (sauce, tomato processing seasoning, flavor seasoning, mixture for cooking, seasoning soy sauce etc.), and processed meat product (meat ham, sausage etc.) and the like.

The content of hydroxylated fatty acid in the food or food additive of the present invention is 5 wt %-90 wt %, preferably 10 wt %-80 wt %, more preferably 20 wt %-70 wt %, based on the total amount of the food or food additive.

The above-mentioned edible oil, food or food additive can be blended with, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, Agaricus and the like.

The above-mentioned edible oils, food or food additive also encompasses those classified in the health food, functional food, food with health claims such as food for specified health uses etc., edible oils, food or food additive with a disease risk reduction indication, food for special dietary uses (e.g., food for patient) and the like.

The homopolymer of hydroxylated fatty acid of the present invention can be used alone or by combining with other substances as a pharmaceutical composition.

The pharmaceutical composition of the present invention can be used as a prophylactic agent for preventing, or a therapeutic agent for treating, improving or suppressing diseases whose symptoms can be improved by hydroxylated fatty acid (e.g., HYA), in animals, for example, obesity, diabetes, lipid metabolism abnormality, hyperlipidemia, fatty liver, inflammatory bowel disease (ulcerative colitis, Crohn's disease, pseudomembranous enteritis etc.), ulcer, irritable bowel syndrome, and various other inflammatory diseases (e.g., gout, arthritis, polyneuritis, polyneuroradiculitis, hepatitis, bronchitis, pneumonia, nephritis, cystitis, periodontal disease, dermatitis, atopic dermatitis etc.).

As used herein, the "animal" includes mammals such as human, dog, cat, rabbit, hamster, rat, mouse, bovine, swine, sheep, horse, donkey, camel and the like.

While the dosage form of the pharmaceutical composition is not particularly limited, for example, powder, granule, pill, soft capsule, hard capsule, tablet, chewable tablet, quick-integrating tablet, syrup, liquid, suspension, suppository, ointment, cream, gel, adhesive preparation, inhalant, injection and the like can be mentioned.

The additives that can be used for formulation of the pharmaceutical composition are not particularly limited. For example, animal and plant oils such as soybean oil, safflower oil, olive oil, germ oil, sunflower oil, beef tallow, sardine oil and the like; polyhydric alcohols such as polyethylene glycol, propylene glycol, glycerol, sorbitol and the like; surfactants such as sorbitan fatty acid ester, sucrose fatty acid ester, glycerol fatty acid ester, polyglycerol fatty acid ester and the like; purified water; excipients such as lactose, starch, crystalline cellulose, D-mannitol, lecithin, gum arabic, sorbitol solution, carbohydrate solution and the like; sweetener, colorant, pH adjuster, flavor and the like can be mentioned. The liquid preparation may be in the form of being dissolved or suspended in water or other suitable medium when it is taken. In addition, the tablet and granule may be coated by a well-known method.

When the pharmaceutical composition is administered in the form of an injection, it is not particularly limited. For example, it is preferably administered intravenously, intraperitoneally, intramuscularly, subcutaneously, transdermally, intra-articularly, intrasynovially, intrathecally, intramedullary, sublingually, intraorally and the like, particularly preferably intravenously or intraperitoneally. The intravenous administration may be any of drip administration and bolus administration.

The content of homopolymer of hydroxylated fatty acid in the pharmaceutical composition is 5 wt %-99.9 wt %, preferably 10 wt %-90 wt %, more preferably 20 wt %-80 wt %, based on the total amount of the pharmaceutical composition.

The dose of the pharmaceutical composition of the present invention or the ingestion amount of the food of the present invention can be appropriately determined according to the age and body weight of the patients or those who ingest same, symptom, administration time, dosage form, administration method, combination of medicaments and the like. For example, when the pharmaceutical composition of the present invention is orally administered, the total amount of the monomer of hydroxylated fatty acid (e.g., HYA) as an active ingredient is 0.02-100 mg/kg body weight, preferably 0.2-50 mg/kg body weight, per day for an adult, or 0.002-50 mg/kg body weight, preferably 0.02-50 mg/kg body weight, by parenteral administration, which can be administered once a day or in several (2-5) portions per day.

When a composition containing the homopolymer of hydroxylated fatty acid of the present invention is used as cosmetics or cosmetics additive, the cosmetics may be, for example, cream, gel, milky lotion, serum, toner, micro emulsion essence, facial mask, foundation, lip rouge, eye shadow, shampoo, conditioner, bathing powder and the like, and may be mixed with a flavor and the like.

The content of homopolymer of hydroxylated fatty acid in the cosmetics or cosmetics additive is 5 wt %-70 wt %, preferably 10 wt %-60 wt %, more preferably 20 wt %-50 wt %, based on the total amount of the cosmetics or cosmetics additives.

When a composition containing the homopolymer of hydroxylated fatty acid of the present invention is used as a feed or feed additive, the feed may be, for example, a pet food, a farming or aquaculture feed additive or the like.

The content of homopolymer of hydroxylated fatty acid in the feed or feed additive is 1 wt %-70 wt %, preferably 3 wt %-50 wt %, more preferably 5 wt %-30 wt %, based on the total amount of the feed or feed additive.

EXAMPLE

The present invention is explained in detail in the following by referring to Examples, which are not to be construed as limitative. The invention may be changed within the scope of the present invention.

$^1$H NMR spectrum was measured using AVANCE III 400 manufactured by Bruker and deuterochloroform as a solvent. The data of $^1$H NMR are reported as chemical shift (δ ppm), multiplicity (s=singlet, d=doublet, t=triplet, q=quartet, m=multiplet, dd=double doublet, dt=double triplet, tt=triple triplet, brs=broad singlet, sep=septet), coupling constant (Hz), integration and allocation.

High resolution mass spectrometry analysis was performed using LCMS (LCMS-2020) manufactured by SHIMADZU Corporation.

The ratio of eluent in chromatography is a volume ratio.

In the following Examples, hydroxylated fatty acid 10-hydroxy-cis-12-octadecenoic acid (HYA) and 10-hydroxy-cis-12,cis-15-octadecadienoic acid (αHYA) used were produced based on the method described in patent document 2 (WO 2013/168310). 13-Hydroxy-cis-9-octadecenoic acid (13HYA) was produced based on the method described in WO 2015/111699. Ricinoleic acid used was a commercially available product. As lipase, lipase AY "Amano" 30SD (derived from *Candida cylindracea*) manufactured by Amano Enzyme Inc. was used.

Example 1

<Production of Homopolymer of 10-Hydroxy-Cis-12-Octadecenoic Acid>

MilliQ water (0.3 mL) was added to 10-hydroxy-cis-12-octadecenoic acid (184 mg) and the mixture was sonicated for 20 sec. Lipase AY "Amano" 30SD (11 mg) was added and the mixture was reacted by stirring at 37° C., 130 rpm for 24 hr. The liquid after the reaction was extracted by the Bligh-Dyer method, and isolated and purified by silica gel chromatography (eluent hexane:diethyl ether:acetic acid=40:60:1) to give a dimer of HYA (9.4 mg), a trimer of HYA (4.7 mg), and a tetramer of HYA (7.9 mg).

dimer of HYA

Rf value=0.30 by silica gel chromatography (eluent hexane:diethyl ether:acetic acid=40:60:1)

$^1$H NMR (CDCl$_3$, 400 MHz): (δ) ppm: 0.89 (t, 6H, J=6.8 Hz), 1.29 (m, 32H), 1.59 (m, 8H), 2.02 (dt, 2H, J=6.2, 7.0 Hz), 2.05 (dt, 2H, J=6.7, 6.9 Hz), 2.22 (dd, 2H, J=7.1, 7.1 Hz), 2.27 (dd, 2H, J=7.3, 7.3 Hz), 2.33 (t, 4H, J=7.5 Hz), 3.64 (tt, 1H, J=5.9, 6.2 Hz), 4.89 (tt, 1H, J=5.9, 6.3 Hz), 5.32 (dt, 1H, J=10.9, 7.3 Hz), 5.39 (dt, 1H, J=11.0, 5.9 Hz), 5.48 (dt, 1H, J=10.9, 7.2 Hz), 5.58 (dt, 1H, J=10.9, 7.3 Hz);

MS(ESI): M$^-$ 577.

trimer of HYA

Rf value=0.38 by silica gel chromatography (eluent hexane:diethyl ether:acetic acid=40:60:1)

$^1$H NMR (CDCl$_3$, 400 MHz): (δ) ppm: 0.89 (t, 9H, J=6.9 Hz), 1.30 (m, 42H), 1.58 (m, 12H), 2.02 (dt, 4H, J=6.4, 7.1 Hz), 2.05 (dt, 2H, J=7.1, 6.5 Hz), 2.22 (dd, 2H, J=6.8, 6.8 Hz), 2.27 (dd, 4H, J=7.5, 7.5 Hz), 2.34 (t, 6H, J=7.5 Hz), 3.62 (tt, 1H, J=5.9, 6.3 Hz), 4.88 (tt, 2H, J=6.2, 6.2 Hz), 5.31 (dt, 2H, J=10.9, 7.3 Hz), 5.39 (dt, 1H, J=10.9, 7.5 Hz), 5.47 (dt, 2H, J=10.9, 7.3 Hz), 5.57 (dt, 1H, J=10.9, 7.3 Hz);

MS(ESI): M$^-$ 857.

tetramer of HYA

Rf value=0.42 by silica gel chromatography (eluent hexane:diethyl ether:acetic acid=40:60:1)

$^1$H NMR (CDCl$_3$, 400 MHz): (δ)ppm: 0.89 (t, 12H, J=6.9 Hz), 1.26 (m, 64H), 1.58 (m, 16H), 2.02 (dt, 6H, J=6.6, 7.2 Hz), 2.05 (dt, 2H, J=6.8, 7.1 Hz), 2.21 (dd, 2H, J=6.9, 6.9 Hz), 2.27 (dd, 6H, J=7.8, 7.8 Hz), 2.34 (t, 8H, J=7.5 Hz), 3.62 (tt, 1H, J=5.9, 6.1 Hz), 4.88 (tt, 3H, J=6.3, 6.1 Hz), 5.31 (dt, 3H, J=10.9, 7.3 Hz), 5.40 (dt, 1H, J=10.9, 7.5 Hz), 5.47 (dt, 3H, J=10.9, 7.3 Hz), 5.57 (dt, 1H, J=10.9, 7.3 Hz);

MS(ESI): M$^+$ (+Na)1161.

The melting point of HYA is about 25° C., and dimer of HYA, trimer of HYA, and tetramer of HYA are liquid at 15° C. and become substances easy to handle.

Example 2

<Confirmation of Formation of Dimer to Decamer of HYA>

MilliQ water (0.3 mL) was added to 10-hydroxy-cis-12-octadecenoic acid (184 mg) and the mixture was sonicated for 20 sec. Thereafter, lipase AY "Amano" 30SD (11 mg) was added and the mixture was reacted by stirring at 37° C., 130 rpm for 24 hr. The fats and oils component alone was extracted from the reaction solution by the Bligh-Dyer method and concentrated by an evaporator. The resulting solution was applied to thin layer chromatography (TLC Silica gel 60 F254; eluent hexane:diethyl ether:acetic acid=40:60:1). The results of thin layer chromatography (365 nm UV radiation) are shown in FIG. 1.

From FIG. 1, the spots where HYAs were polymerized could be confirmed. From the number of spots, it could be confirmed that HYAs became a dimer to a decamer.

The Rf value of each spot is as follows.

dimer of HYA: 0.30
trimer of HYA: 0.38
tetramer of HYA: 0.42
pentamer of HYA: 0.46
hexamer of HYA: 0.49
heptamer of HYA: 0.52
octamer of HYAr: 0.55
nonamer of HYA: 0.56
decamer of HYA: 0.59

Example 3

<Comparison of Oxidation Stability of Hydroxylated Fatty Acid and Homopolymer Mixture Thereof>

The oxidation stability was compared between the reaction extract (homopolymer mixture) obtained in Example 1 and HYA. The oxidation reaction was performed using NAD$^+$ as an electron receptor in the presence of hydroxylated fatty acid dehydrogenase (CLA-DH) (S. Kishino et al., Polyunsaturated fatty acid saturation by gut lactic acid bacteria affecting host lipid composition. Proc. Natl. Acad. Sci. USA, 110(44), 17808-17813, 2013).

The reaction mixture (3 mL) contained CLA-DH-expressing *Escherichia coli* cell-free extract (150 μL, derived from 50 mg *Escherichia coli* wet cells) as hydroxylated fatty acid dehydrogenase, 4 mM NAD$^+$, 150 μL of ethanol, and 0.48 mM (0.143 mg/mL) HYA or equal amount (0.143 mg/mL) of a homopolymer mixture as a substrate, and the reaction was started by the addition of hydroxylated fatty acid dehydrogenase and performed at 37° C. for about 6 min. The control did not contain a substrate. The progress of oxidation was quantified by measuring the change in absorbance at 340 nm of NADH amount produced by the oxidation of the substrate (the molecular absorption coefficient of NADH was 6.3×10$^3$ L·mol$^{-1}$ cm$^{-1}$).

Figure 2:
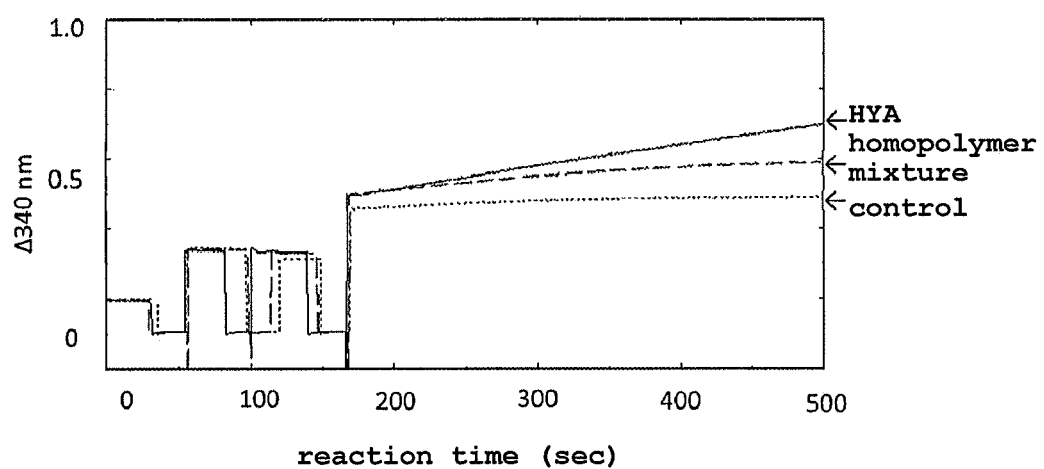
FIG. 2 is a graph showing the results of Example 3 (comparison of oxidation reaction rate between HYA and homopolymer mixture thereof).

The results are shown in FIG. 2. HYA was oxidized at a rate of 2.9 μM/min, and the oxidation rate of the homopolymer mixture was 1.6 μM/min, showing a decrease to about 55% of the oxidation rate of HYA. Therefore, it was confirmed that the oxidation stability of hydroxylated fatty acid increased by homopolymerization to afford a stable substance.

Example 4

<Confirmation of Formation of Homopolymer of αHYA, 13HYA, Ricinoleic Acid>

MilliQ water (0.3 mL) was added to αHYA, 13HYA, or ricinoleic acid (each 184 mg) and the mixture was sonicated for sec. Thereafter, lipase AY "Amano" 30SD (11 mg) was added and the mixture was reacted by stirring at 37° C., 130 rpm for 24 hr. The fats and oils component alone was extracted from the reaction solution by the Bligh-Dyer method and concentrated by an evaporator. The resulting solution was applied to thin layer chromatography (TLC Silica gel 60 F254; eluent hexane:diethyl ether:acetic acid=40:60:1). The results of thin layer chromatography (365 nm UV radiation) are shown in FIG. 3.

Figure 3:
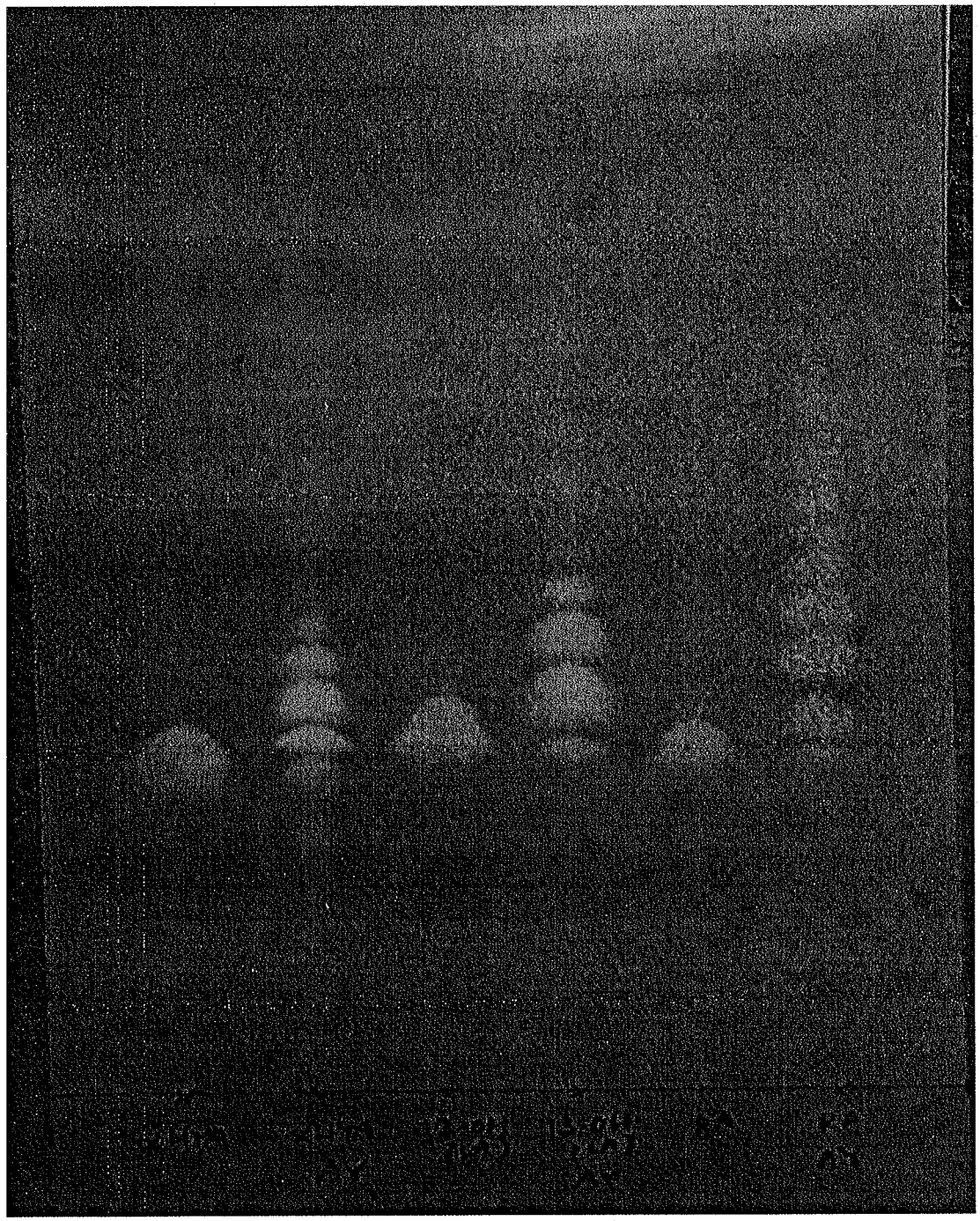
FIG. 3 is a photograph showing the results of thin layer chromatography in Example 4.

From FIG. 3, the spots where αHYA, 13HYA, ricinoleic acid were polymerized could be confirmed. From the number of spots, it could be confirmed that each homopolymer was a dimer to a heptamer. The dimer to decamer can be confirmed by increasing the spot amount and the like.

The Rf value of each spot in FIG. 3 is as follows.
monomer of αHYA: 0.31
dimer of αHYA: 0.34
trimer of αHYA: 0.38
tetramer of αHYA: 0.43
monomer of 13HYA: 0.33
dimer of 13HYA: 0.39
trimer of 13HYA: 0.44
tetramer of 13HYA: 0.49
monomer of ricinoleic acid: 0.33
dimer of ricinoleic acid: 0.37
trimer of ricinoleic acid: 0.42
tetramer of ricinoleic acid: 0.47

The dimer, trimer and tetramer of αHYA, the dimer, trimer and tetramer of 13HYA, and the dimer, trimer and tetramer of ricinoleic acid are respectively represented by the following formulas.

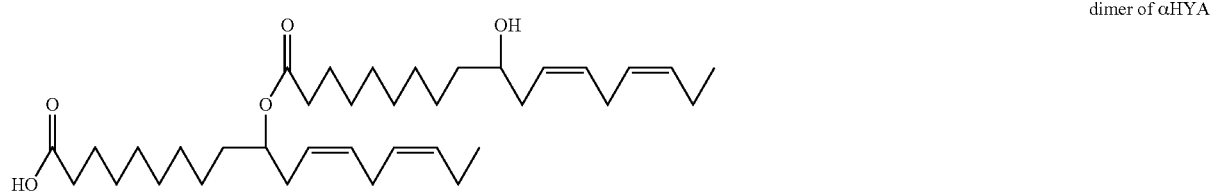

dimer of αHYA

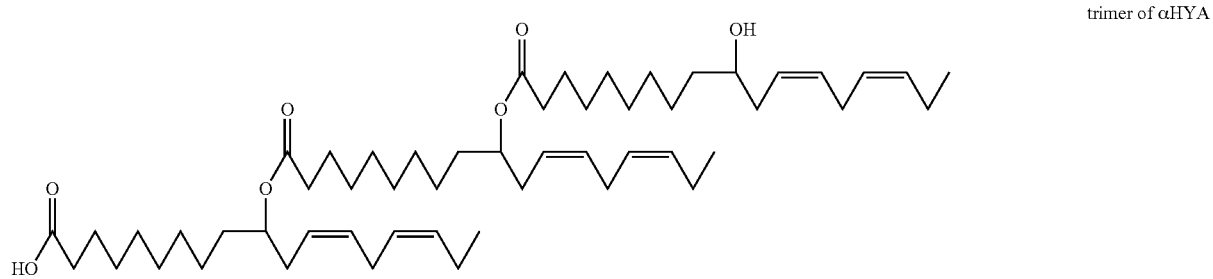

trimer of αHYA

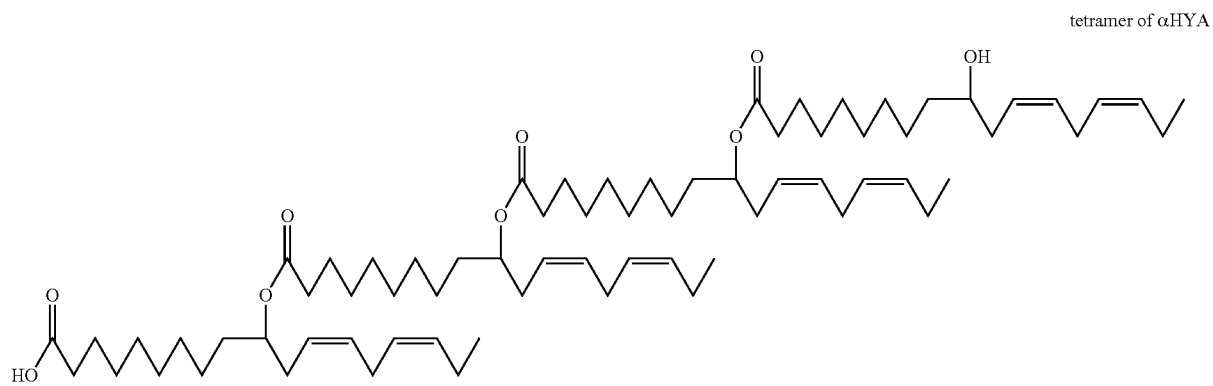

tetramer of αHYA

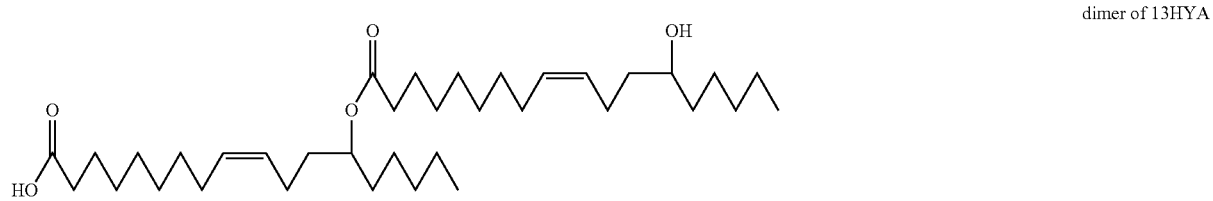

dimer of 13HYA

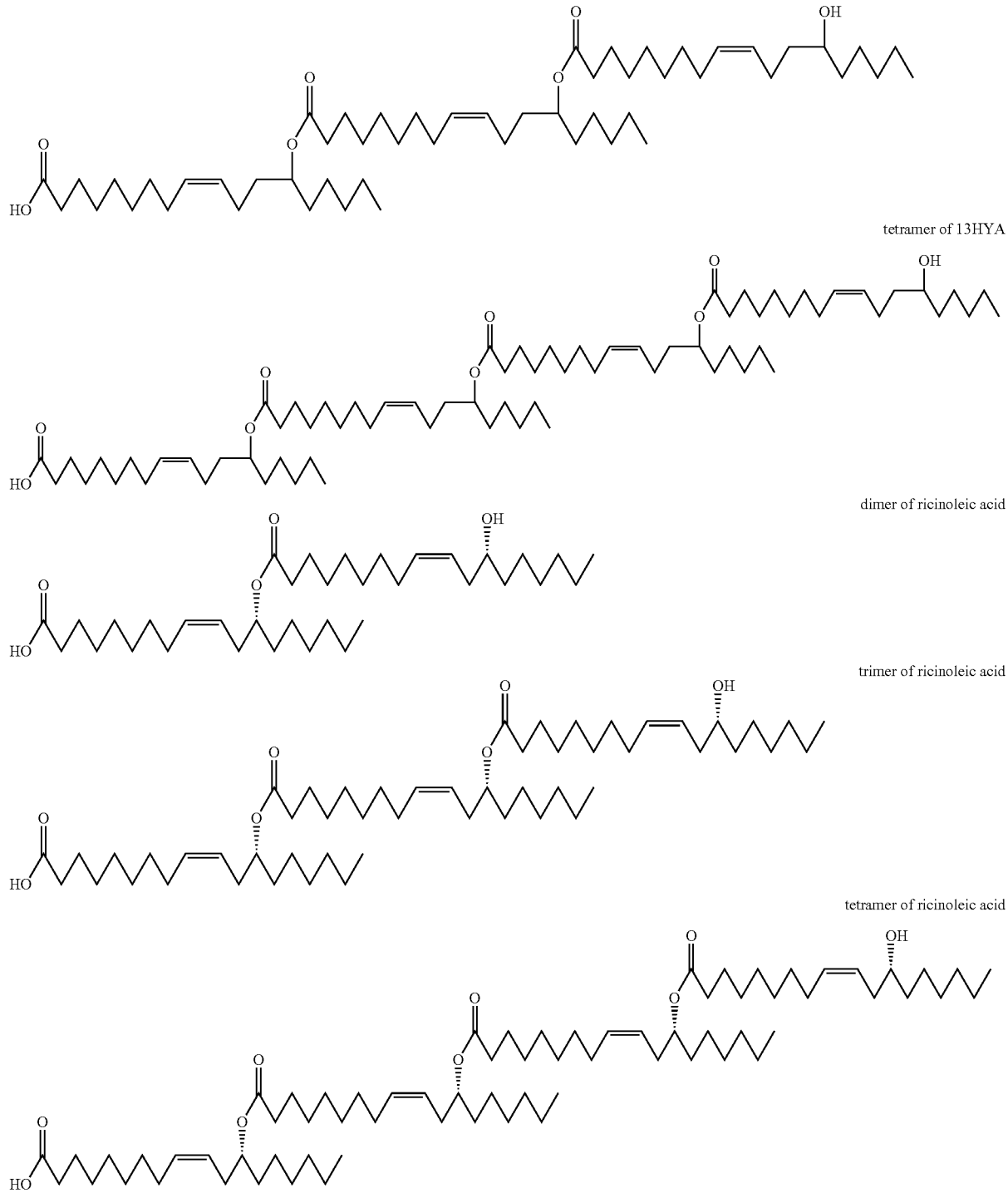

trimer of 13HYA tetramer of 13HYA dimer of ricinoleic acid trimer of ricinoleic acid tetramer of ricinoleic acid From the results of Example 4, it was shown that a homopolymer can be produced in the same manner as in HYA even when hydroxylated fatty acid (αHYA) having two or more double bonds, hydroxylated fatty acid (13HYA) having a hydroxyl group at the 13-position, hydroxylated fatty acid (ricinoleic acid) having a hydroxyl group at the 12-position was used as a substrate.

From the above results, hydroxylated fatty acid can be converted to a homopolymer by the method of the present invention, and the homopolymer is a novel substance and has become a further stabilized substance.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

This application is based on patent application No. 2017-167595 filed in Japan (filing date: Aug. 31, 2017), the contents of which are incorporated in full herein.

INDUSTRIAL APPLICABILITY

According to the method of the present invention, various hydroxylated fatty acids can be converted to homopolymers of hydroxylated fatty acids. Thus, the method is also extremely useful for multimerizing and further stabilizing hydroxylated fatty acid. In addition, the homopolymer of hydroxylated fatty acid of the present invention is used by combining with, for example, medicament, food, and cosmetics.

The invention claimed is:

1. A method for producing a homopolymer of hydroxylated fatty acid, comprising polymerizing the hydroxylated fatty acid by using an enzyme, wherein the hydroxylated fatty acid is
10-hydroxy-cis-12-octadecenoic acid,
10-hydroxy-cis-12,cis-15-octadecadienoic acid,
10-hydroxy-cis-6,cis-12-octadecadienoic acid,
10-hydroxy-cis-6,cis-12,cis-15-octadecatrienoic acid,
10-hydroxy-cis-15-octadecenoic acid,
10-hydroxy-cis-6-octadecenoic acid,
10-hydroxy-cis-6,cis-15-octadecadienoic acid,
10-hydroxy-trans-11-octadecenoic acid,
10-hydroxy-trans-11,cis-15-octadecadienoic acid,
10-hydroxy-cis-6,trans-11-octadecadienoic acid,
10-hydroxy-cis-6,trans-11,cis-15-octadecatrienoic acid,
13-hydroxy-cis-9-octadecenoic acid,
13-hydroxy-cis-9,cis-15-octadecadienoic acid,
13-hydroxy-cis-6,cis-9-octadecadienoic acid,
13-hydroxy-cis-6,cis-9,cis-15-octadecatrienoic acid,
13-hydroxy-cis-5,cis-9-octadecadienoic acid, or
13-hydroxy-trans-5,cis-9-octadecadienoic acid,
a fatty acid having 20 carbon atoms and a hydroxyl group at the 12-position or the 15-position,
a fatty acid having 14 or 16 carbon atoms and a hydroxyl group at the 10-position, or
a fatty acid having 22 carbon atoms and a hydroxyl group at the 14-position.

2. The method according to claim 1, wherein the enzyme is a lipase.

3. The method according to claim 1, wherein the enzyme is a lipase derived from a microorganism belonging to the genus *Candida*.

4. The method according to claim 1, wherein the enzyme is a lipase derived from *Candida cylindracea* or *Candida rugosa*.

5. The method according to claim 1, wherein the homopolymer of hydroxylated fatty acid is a dimer to decamer.

6. The method according to claim 1, wherein the hydroxylated fatty acid is a fatty acid having 20 carbon atoms and a hydroxyl group at the 12-position or the 15-position.

7. The method according to claim 1, wherein the hydroxylated fatty acid is a fatty acid having 14 or 16 carbon atoms and a hydroxyl group at the 10-position.

8. The method according to claim 1, wherein the hydroxylated fatty acid is
10-hydroxy-cis-12-octadecenoic acid,
10-hydroxy-cis-12,cis-15-octadecadienoic acid,
10-hydroxy-cis-6,cis-12-octadecadienoic acid,
10-hydroxy-cis-6,cis-12,cis-15-octadecatrienoic acid,
10-hydroxy-cis-15-octadecenoic acid,
10-hydroxy-cis-6-octadecenoic acid,
10-hydroxy-cis-6,cis-15-octadecadienoic acid,
10-hydroxy-trans-11-octadecenoic acid,
10-hydroxy-trans-11,cis-15-octadecadienoic acid,
10-hydroxy-cis-6,trans-11-octadecadienoic acid,
10-hydroxy-cis-6,trans-11,cis-15-octadecatrienoic acid,
13-hydroxy-cis-9-octadecenoic acid,
13-hydroxy-cis-9,cis-15-octadecadienoic acid,
13-hydroxy-cis-6,cis-9-octadecadienoic acid,
13-hydroxy-cis-6,cis-9,cis-15-octadecatrienoic acid,
13-hydroxy-cis-5,cis-9-octadecadienoic acid, or
13-hydroxy-trans-5,cis-9-octadecadienoic acid.

9. The method according to claim 6, wherein the hydroxylated fatty acid is
12-hydroxy-cis-14-eicosenoic acid,
12-hydroxy-cis-14,cis-17-eicosadienoic acid,
12-hydroxy-cis-8,cis-14-eicosadienoic acid,
12-hydroxy-cis-5,cis-8-eicosadienoic acid,
12-hydroxy-cis-8,cis-14,cis-17-eicosatrienoic acid, or
12-hydroxy-cis-5,cis-8,cis-14-eicosatrienoic acid.

10. The method according to claim 6, wherein the hydroxylated fatty acid is
15-hydroxy-cis-11-eicosenoic acid,
15-hydroxy-cis-11,cis-17-eicosadienoic acid,
15-hydroxy-cis-8,cis-11-eicosadienoic acid,
15-hydroxy-cis-8,cis-11,cis-17-eicosatrienoic acid,
15-hydroxy-cis-5,cis-8,cis-11-eicosatrienoic acid,
15-hydroxy-cis-5,cis-11-eicosadienoic acid, or
15-hydroxy-cis-5,cis-11,cis-17-eicosatrienoic acid.

11. The method according to claim 1, wherein the hydroxylated fatty acid is
10-hydroxytetradecanoic acid,
10-hydroxyhexadecanoic acid, or
14-hydroxy-cis-4,cis-7,cis-10,cis-16,cis-19-docosapentaenoic acid.

12. A homopolymer as a dimer to a decamer of any one hydroxylated fatty acid selected from the following hydroxylated fatty acids:
10-hydroxy-cis-12-octadecenoic acid,
10-hydroxy-cis-12,cis-15-octadecadienoic acid,
10-hydroxy-cis-6,cis-12-octadecadienoic acid,
10-hydroxy-cis-6,cis-12,cis-15-octadecatrienoic acid,
10-hydroxy-cis-15-octadecenoic acid,
10-hydroxy-cis-6-octadecenoic acid,
10-hydroxy-cis-6,cis-15-octadecadienoic acid,
10-hydroxy-trans-11-octadecenoic acid,
10-hydroxy-trans-11,cis-15-octadecadienoic acid,
10-hydroxy-cis-6,trans-11-octadecadienoic acid,
10-hydroxy-cis-6,trans-11,cis-15-octadecatrienoic acid,
13-hydroxy-cis-9-octadecenoic acid,
13-hydroxy-cis-9,cis-15-octadecadienoic acid,
13-hydroxy-cis-6,cis-9-octadecadienoic acid,
13-hydroxy-cis-6,cis-9,cis-15-octadecatrienoic acid,
13-hydroxy-cis-5,cis-9-octadecadienoic acid,
13-hydroxy-trans-5,cis-9-octadecadienoic acid,
12-hydroxy-cis-14-eicosenoic acid,
12-hydroxy-cis-14,cis-17-eicosadienoic acid,
12-hydroxy-cis-8,cis-14-eicosadienoic acid,
12-hydroxy-cis-5,cis-8-eicosadienoic acid,
12-hydroxy-cis-8,cis-14,cis-17-eicosatrienoic acid,
12-hydroxy-cis-5,cis-8,cis-14-eicosatrienoic acid,
15-hydroxy-cis-11-eicosenoic acid,
15-hydroxy-cis-11,cis-17-eicosadienoic acid,
15-hydroxy-cis-8,cis-11-eicosadienoic acid,
15-hydroxy-cis-8,cis-11,cis-17-eicosatrienoic acid,
15-hydroxy-cis-5,cis-8,cis-11-eicosatrienoic acid,
15-hydroxy-cis-5,cis-11-eicosadienoic acid,
15-hydroxy-cis-5,cis-11,cis-17-eicosatrienoic acid,
10-hydroxytetradecanoic acid,
10-hydroxyhexadecanoic acid, and
14-hydroxy-cis-4,cis-7,cis-10,cis-16,cis-19-docosapentaenoic acid.

13. The homopolymer according to claim 12, wherein the homopolymer is a dimer, a trimer or a tetramer of 10-hydroxy-cis-12-octadecenoic acid represented by the formula

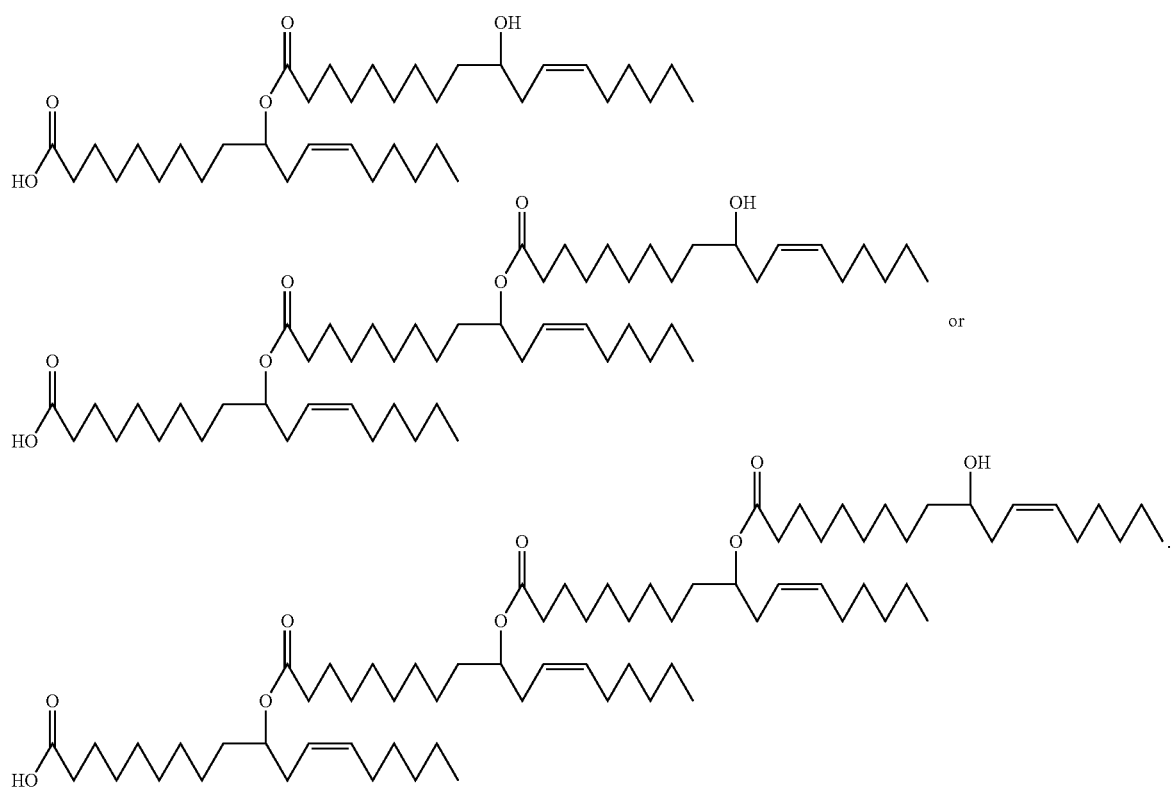
14. A composition comprising the homopolymer according to claim 12.
15. A composition comprising the homopolymer according to claim 13.
16. The method according to claim 1, wherein the hydroxylated fatty acid is a fatty acid having 22 carbon atoms and a hydroxyl group at the 14-position.
* * * * *